US010792255B2

(12) United States Patent
Chang et al.

(10) Patent No.: US 10,792,255 B2
(45) Date of Patent: Oct. 6, 2020

(54) RECONSTITUTED APOLIPOPROTEIN B LIPOPARTICLE, A PREPARATION METHOD AND USES THEREOF

(71) Applicant: National Chiao Tung University, Hsinchu (TW)

(72) Inventors: Chia-Ching Chang, Hsinchu (TW); Gong-Shen Chen, Taipei (TW); Tsai-Mu Cheng, Taipei (TW); Hsueh-Liang Chu, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 310 days.

(21) Appl. No.: 15/481,027

(22) Filed: Apr. 6, 2017

(65) Prior Publication Data

US 2017/0209388 A1   Jul. 27, 2017

Related U.S. Application Data

(62) Division of application No. 14/324,131, filed on Jul. 4, 2014, now abandoned.

(30) Foreign Application Priority Data

Dec. 27, 2013   (TW) .............................. 102148633 A

(51) Int. Cl.
| | | |
|---|---|---|
| *A61B 5/055* | (2006.01) | |
| *A61K 9/51* | (2006.01) | |
| *A61K 49/18* | (2006.01) | |
| *A61K 31/09* | (2006.01) | |

(52) U.S. Cl.
CPC .......... *A61K 9/5169* (2013.01); *A61K 9/5123* (2013.01); *A61K 31/09* (2013.01); *A61K 49/1866* (2013.01)

(58) Field of Classification Search
None
See application file for complete search history.

(56) References Cited

U.S. PATENT DOCUMENTS 5,652,339 A * 7/1997 Lerch ................... C07K 14/775
530/359
2008/0253960 A1* 10/2008 Zheng ................ A61K 41/0071
514/1.1

OTHER PUBLICATIONS

Mahley et al. (J. Lipid Res. 1984, 25, 1277-1294).*
Cardin et al. (Biochem. 1982, 21, 4503-4511).*
Chu, H-L. Refolding/Reconstitution of Apolipoprotein B and its Application, National Chiao Tung University Institutional Repository 2012, see abstract. (http-:11140.113.39.130/cdrfb3/record /nctu/ #GT079629801).*
Reynold (Annals New York Academy of Sciences 1980 p. 174-186).*
Segrest et al. (J. Lipid Res. 2001, 42, 1346-1367).*
Chang et al. (Phys. Rev. E 2004, 70, 011904-1 to 011904-8).*
Chang et al. (Chinese J. Phys. 2007, 45, 693-702).*
Firestone, et al., (J. Med. Chem. 1984, 27, 1037-1043).
Nikanjam, et al., (J. Controlled Release 2007, 124, 163-171).

* cited by examiner

*Primary Examiner* — Michael G. Hartley
*Assistant Examiner* — Melissa J Perreira
(74) *Attorney, Agent, or Firm* — Mintz Levin Cohn Ferris Glovsky and Popeo, P.C.; Peter F. Corless; Joohee Lee

(57) ABSTRACT

The present invention provides a method for preparing a reconstituted apolipoprotein B lipoparticle and the method comprises steps of (a) dissolving an apolipoprotein B and a lipid in a first buffer containing 2 M to 8 M urea and 1 wt % to 15 wt % amphiphilic compounds to form a mixture; and (b) dialyzing the mixture against a second buffer containing 0 M to 2M urea and 0 wt % to 0.5 wt % amphiphilic compounds for 1 to several times for lowering concentrations of the urea and the amphiphilic compounds in the mixture. The present invention further provides an apolipoprotein B lipoparticle and a use for the production of an apolipoprotein B lipoparticle used for delivering a hydrophobic substance.

11 Claims, 12 Drawing Sheets

RECONSTITUTED APOLIPOPROTEIN B LIPOPARTICLE, A PREPARATION METHOD AND USES THEREOF

CROSS REFERENCE TO RELATED APPLICATIONS

This application is a divisional of U.S. application Ser. No. 14/324,131, filed Jul. 4, 2014, which claims the benefit of Taiwan Application Ser. No. 102148633, filed Dec. 27, 2013, the contents of which are hereby incorporated by reference in their entirety.

BACKGROUND OF THE INVENTION

1. Field of the Invention

The present invention relates to a reconstituted apolipoprotein B lipoparticle, and a preparation method thereof, and more particularly to a reconstituted apolipoprotein B lipoparticle for delivering hydrophobic substances.

2. Description of Related Art

Low density lipoprotein is composed of a single apolipoprotein B and several lipids (including cholesteryl ester (CE)), free cholesterol (FC), triglyceride (TG), and phospholipid (PL), and its size is approximately 18 to 25 nanometer (nm). Apolipoprotein B not only synthesizes low-density lipoproteins (hereinafter referred to LDL), it is also the major protein of very low-density lipoproteins (VLDL) and chylomicrons. In the human body, apolipoprotein B has two major forms: apolipoprotein B-100 (apoB-100) of full length, consisting of 4563 amino acids, and apolipoprotein B-48 with 48% N-terminal sequence of the apolipoprotein by mRNA modification contains 2153 amino acids. Apolipoprotein B-100 is present in the liver and then synthesizes VLDL and LDL in the liver, while apolipoprotein B-48 synthesizes chylomicron in the small intestine. Physiologically, LDL plays a role in metabolism of lipids, which transports cholesterol and triglyceride from liver to other tissues for usage of cell (more than ⅔ cholesterol is transported via this system). Aapolipoprotien B can be recognized via extracellular LDL receptors and LDL can be uptook. The apolipoprotein B contains protein domains with □-helical and □-sheet and the protein domain can be classified as □□1, □1, □2, □2, and □3).

Apolipoprotein B on the LDL is recognized by the LDL receptors and internalized in the cell. When LDL is transferred into cells through endocytosis, the endosome is formed then fused with lysozyme. In this process, the LDL is degraded to cholesterols, amino acids, and fatty acids. The degraded cholesterol is converted to steroid hormones, or used for synthesis of cell membranes or stored in the cell, while LDL receptor is recycled to the surface of the cell.

Several researches have shown that LDL receptors are overexpressed in various cancer cells. For instance, glioblastoma multiforme (GBM), a type of brain cancer, has higher expressions for LDL receptors compared to normal brain tissues. As a result, LDL-based drug delivery system can be applied to target therapy of cancers.

LDL is composed of apolipoprotein B and lipids. However, some synthesis pathways for LDL still remained unknown. Moreover, there are a lot of drugs that are lipophilic and hard to be transported in the physiological condition of the human body.

SUMMARY OF THE INVENTION

The objective of present invention is to understand the mechanisms for LDL synthesis through refolding/reconstitution of LDL. Low density lipoprotein plays a role in the transportation of lipids in the human body, and moreover as the characteristics such a being stable, high hydrophilic, and recognizable and internalized by the receptors, inventors attempted to utilize a reconstituted low density lipoprotein as a new drug carrier.

The present invention provides a method for preparing a reconstituted apolipoprotein B lipoparticle, comprising steps of: a) dissolving apolipoprotein B and lipid in a first buffer containing 1 wt % to 15 wt % amphiphilic compounds and 2M to 8M urea to from a mixture; and b) dialyzing the mixture against a second buffer for 1 to several times to reduce the concentrations of the urea and the amphiphilic compound in the mixture, wherein the second buffer contains 0M to 2M urea and 0 wt % to 0.5 wt % amphiphilic compounds.

In one embodiment of the present invention, the method further comprises steps of dissolving a hydrophobic substance in a buffer containing the same composition of the first buffer of step a), and filtering the buffer containing the hydrophobic substance, followed by adding it to the mixture of step a).

In another embodiment of the present invention, the hydrophobic substance and lipid are dissolved in the above-mentioned first buffer to form a mixture containing hydrophobic substance and lipid, followed by adding the apolipoprotein B dissolved in the first buffer into the mixture containing the hydrophobic substance and lipid.

In one embodiment of the prevent invention, preferably, the hydrophobic substance is selected from a contrast medium or a lipophilic drug. Preferably, the contrast medium is at least one selected from the group consisting of superparamagnetic iron oxide nanoparticle, mangafodipir, gadoxetic acid, gadopentetic acid, gadobenic acid, gadoteric acid and vistarem. Preferably, the lipophilic drug is at least one selected from the group consisting of tetra-O-methyl nordihydroguaiaretic acid (hereinafter referred to M4N), paclitaxel and doxorubincin.

In one embodiment of the present invention, preferably, the pH value of the first buffer is 11. Preferably, the pH value of the second buffer ranges from 8.8 to 11.

In one embodiment of the present invention, preferably, the above-mentioned apolipoprotein B is selected from natural apolipoprotein B or reconstituted apolipoprotein B. Preferably, the apolipoprotein B is at least one selected from the group consisting of apolipoprotein B-100, B-29 and B-48.

In one embodiment of the present invention, preferably, the lipid is at least one selected from the group consisting of phospholipid, cholesterol and triglyceride.

In one embodiment of the present invention, preferably, the amphiphilic compound is selected from non-ionic surfactant or bile acid. Preferably, the non-ionic surfactant is Triton X-100 and the bile acid is deoxycholic acid.

The present invention further provides a reconstituted apolipoprotein B lipoparticle, and it comprises an outer layer composed of apolipoprotein B and lipid and hydrophobic core, wherein the outer layer comprises at least one of apolipoprotein B and the inner core comprises at least one of hydrophobic substance.

In one embodiment of the present invention, preferably, the above lipoprotein B is selected from natural apolipoprotein B or reconstituted apolipoprotein B. Preferably, the apolipoprotein B is at least one selected from the group consisting of apolipoprotein B-100, B-29 and B-48.

In one embodiment of the present invention, preferably, the lipid is at least one selected from the group consisting of phospholipid, cholesterol and triglyceride.

In one embodiment of the present invention, preferably, the hydrophobic substance is selected from a contrast medium or a lipophilic drug. Preferably, the contrast medium is at least one selected from the group consisting of superparamagnetic iron oxide nanoparticle, mangafodipir, gadoxetic acid, gadopentetic acid, gadobenic acid, gadoteric acid and vistarem. Preferably, the lipophilic drug is at least one selected from the group consisting of M4N, paclitaxel and doxorubincin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Figure 1:
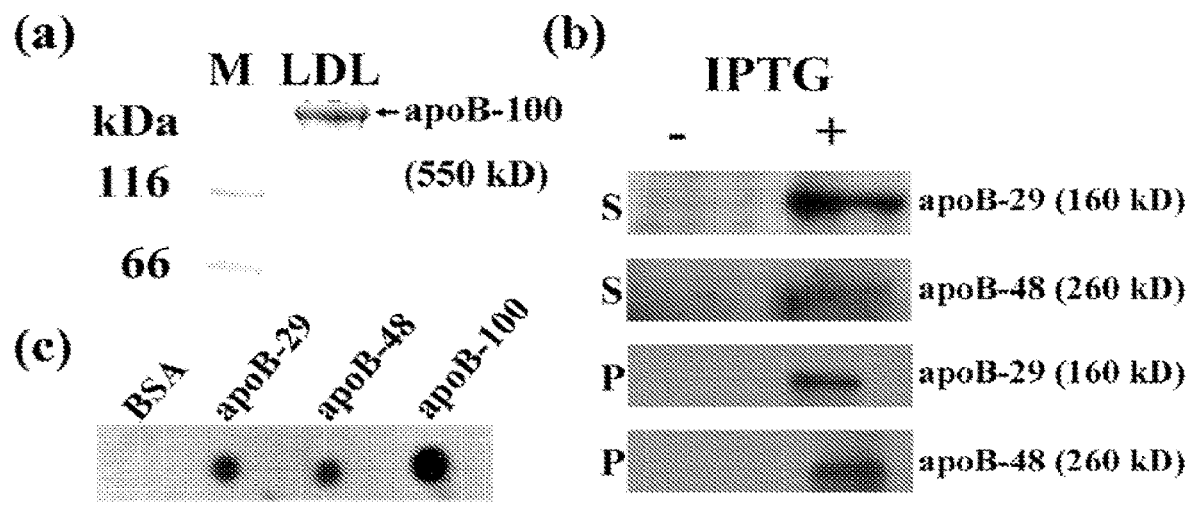
FIG. 1 shows the extraction of LDL and the preparation of apolipoprotein B-29/B-48. (a) Extraction result of LDL; (b) Expressions of apolipoprotein B-29/B-48 in prokaryotic expression system induced by IPTG. S represents the supernatant, while P represents the precipitate. (c) apolipoprotein B-29/B-48 were isolated by ultracentrifugation (density is 1.08 g/ml). BSA is the control group.

The following specific examples are used for illustrating the present invention. A person skilled in the art can easily conceive the other advantages and effects of the present invention. The present invention can also be implemented by different specific cases be enacted or application, the details of the instructions can also be based on different perspectives and applications in various modifications and changes do not depart from the spirit of the creation.

The present invention provides a method for preparing a reconstituted apolipoprotein B lipoparticle (hereinafter referred to rABL), comprising steps of: a) dissolving apolipoprotein B in a first buffer containing 1 wt % to 15 wt % amphiphilic compounds and 2M to 8M urea to form a mixture; and b) dialyzing the mixture against a second buffer for 1 to 5 times to reduce the concentrations of the urea and the amphiphilic compound in the mixture, wherein the concentration of urea ranges from 0 to 2M and the concentration of the amphiphilic compound ranges from 0 to 0.5 wt % in the second buffer. In one embodiment, the first buffer containing 2M to 8M urea and 0 wt % to 0.5 wt % amphiphilic compound is referred as a denaturing buffer while the second buffer containing 0M to 2M urea and 0 wt % to 0.5 wt % amphiphilic compound is referred as a folding buffer. The different concentrations of urea and amphiphilic compound in the first and second buffer can denature protein and lipid, but the solubility of protein and lipid in the denaturing buffer formulated by low concentrations of urea and amphiphilic compound is lower.

The present invention further provides a reconstituted apolipoprotein B lipoparticle, and it comprises an outer layer composed of apolipoprotein B and lipid and an inner core, wherein the outer layer contains at least one of apolipoprotein B while the inner core contains at least one of hydrophobic substance.

The present invention provides a use for the production of a reconstituted apolipoprotein B lipoparticle used for delivering hydrophobic substances.

As used in the present invention, the term "quasi-static over-critical folding path" refers that replacement process of solutions is slow or replacement factor of solutions is minimal during protein folding process and both of the process are approximately equilibrium are called "quasi-static". The over-critical folding path means that multi-steps replacement of solutions allows protein folding process exhibits over-critical point successive reaction.

As used in the present invention, the term "superparamagnetic iron oxide nanoparticle (hereinafter referred to SPIO)" refers that magnetism is created under magnetic field. When the external magnetic field disappears, the magnetism disappears. This property prevents aggregation of the superparamagnetic iron oxide. Superparamagnetic iron oxide nanoparticle can be prepared by precipitation, hydrothermal method and chemical reduction method, in which the superparamagnetic iron oxide nanoparticle prepared by chemical reduction method has preferred uniform particle size but the product is organic phase and could not be dissolved in aqueous solution. If the product is applied in biomedical aspect, moderate modification is required. Recently, many studies have attempted to use superparamagnetic iron oxide nanoparticle as a contrast medium for magnetic resonance imaging (hereinafter referred to MRI), since the superparamagnetic iron oxide nanoparticle has the property of not easily aggregating and which can lower the false signals produced by the contrast medium. Therefore, superparamagnetic iron oxide nanoparticle has a potential used as a good contrast medium. Apart from that, superparamagnetic iron oxide nanoparticle have been also studied its potential for drug delivery and magnetocaloric effect. In the present invention, the superparamagnetic iron oxide nanoparticles without surface modification have been used to perform the experiment of reconstituted apolipoprotein B lipoparticles.

As used in the present invention, the term "tetra-O-methyl nordihydroguaiaretic acid (hereinafter referred to M4N)" refers a non-toxic compound extracted and purified from Zygophyllaceae. Under the condition for long-term feeding the mice with M4N, it was not found any obvious weight changes or mortality in mice. Functionally, M4N is found to inhibit transcription of HIV virus and leads cancer cell death via inhibiting Sp 1 transcription factor. In cancer cells, M4N binds to deoxyribonucleic acid sequence full with G/C and allows the cell growth retaining in G2/M stage. Besides, M4N can also inhibit the expressions of cyclin-dependent kinase (hereinafter referred to CDC2) and suvivin to cause cancer cell death. In the present invention, M4N is used as a hydrophobic drug and tested the possibility of encapsulating M4N into the reconstituted apolipoprotein B packaged in the reconstituted apolipoprotein B lipoparticle.

As used in the present invention, the term "paclitaxel" refers that it is first extracted from the bark of the Pacific yew and has been extensively used in the treatment of cancer, in which the mechanism is to stabilize the produced microtubules during cell division and the microtubule could not be degraded so as to lead the cell division incomplete and finally cell death. However, due to the highly hydrophobic property of paclitaxel, a solubilizing agent is required. The common solubilizing agent is a mixture of cremophor and dehydrated alcohol. Although this mixture can assist paclitaxel dissolve and reach to the target, but it easily cause allergic reaction, leading to undesired side effects during administration of drug. In view of this, Food and Drug Administration (FDA) in U.S, 2005, preferentially approved nanoparticle albumin-bound paclitaxel. Since the nanoparticle albumin-bound pacltixel is embedded by albumin and has the particle size of about 130 nm thereby it can be dissolved in water. In addition, cancer cells need large amount of nutrients including albumin, and thus the nanoparticle albumin-bound paclitaxel can easily enter cancer cells via this mechanism and leads cell death.

EXAMPLE 1

Materials

All chemicals, unless otherwise noted, were purchased from Merck (Rahway, N.J.) or Sigma (St. Louis, Mo.). Human serum was obtained from a healthy volunteer using a protocol approved by the Mackay Memorial Hospital Institutional Review Board (IRB No. 10MMHIS082). Specific pathogen-free, 4-5 weeks old BALB/c mice were purchased from the National Laboratory Animal Center (Taipei, Taiwan). All experiments were carried out in accordance with the Academia Sinica Animal care and Use Committee guideline. Non-coating 2 nm, superparamagnetic iron oxide nanoparticles (hereinafter referred to SPIONPs) can be synthesized or purchased. M4N can be synthesized or purchased. Anti-apoB (C1.4, monoclonal antibody), anti-LDLR, anti-p53 and anti-Erk antibodies were purchased from Santa Cruz Biotechnology Inc. (Santa Cruz, Calif.); anti-apoB polyclonal antibody was purchased from Roche (Branford Conn.); cy3-conjugated secondary antibody was purchased from Jackson Immuno Research Laboratories (West Grove, Pa.); anti-p-p53 (ser-15), anti-p-Erk, anti-p38 and anti-p-p38 were purchased from Cell Signaling Technology (Beverly, Mass.); anti-caspase 3 antibody was purchased from Abcam (Cambridge, UK); Hoechst 33342 was purchased from Invitrogen (Carlsbad, Calif.); anti-3-hydroxy-3-methyl-glutaryl-coenezyme A reductase (HMGR) antibody was purchased from Millipore Corporation (Billerica, Mass.); phalloidin-conjugated antiactin antibody was purchased from Molecular Probe, Life Technologies (New York); cholesterol assay kit was purchased from Cayman Chemical Company (Ann Arbor, Mich.).

EXAMPLE 2

Purification of Low Density Lipoprotein

Whole bloods were centrifuged at 5000×g for 10 mins for separating blood cells and plasma. After collecting plasma, very low density lipoprotein was removed by centrifugation at 45000×g for 16 hrs. Since the density of LDL in a human body ranges from 1.060 to 1.063 g/ml, LDL was then adjusted to such density range using potassium bromide (KBr) and purified by centrifugation at 45000×g for 20 hrs.

EXAMPLE 3

Isolation of Lipoprotein B-100

The purified LDL was delipidated by an ice-cold methanol/ether mixture (methanol:ether=3:1, -80° C.), followed by mixed. The mixture was centrifuged at 3000×g for 5 mins and the precipitants were the isolated lipoprotein B-100.

EXAMPLE 4

Preparation of Lipoprotein B-29 and Lipoprotein B-48

The selected strains containing pET24-apoB29/pET24-apoB48 were cultivated in LB medium until the growth state was reached, followed by adding IPTG to induce protein expression of lipoprotein B-29 and lipoprotein B-48. After the induced strains were lysed by high pressure disruptor, centrifugation was performed to separate the supernatants and the precipitants. The density of the supernatants was adjusted to 1.08 g/ml by KBr, followed by isolating and purifying lipoprotein B-29 and lipoprotein B-48 by ultra centrifugation at 45000×g for 20 hrs.

EXAMPLE 5

Quantification of Cholesterol and Lipoprotein B

The Bradford method was used to determine the concentration of lipoprotein B. A standard calibration curve was obtained using bovine serum albumin (BSA) as a reference protein. The concentration of cholesterol was determined by the cholesterol quantification kit. In LDL, the percentage of cholesterol was kept constant and therefore can be used to calculate the concentration of lipid in the LDL.

EXAMPLE 6

Reconstitution of Apolipoprotein B-100

2 milligrams (mg) of delipidated apolipoprotein B-100 and 6.5 mg of lipids were dissolved in separate Eppendorf tubes containing 1 mL of denaturing buffer listed in Table 1. After filtering through 0.22 μm membrane, both of apolipoprotein B-100 and lipids were mixed gently at 4° C. for 1 h. According to the "quasi-static over-critical folding path" method, the mixture was transferred into a dialysis tube and dialyzed against a series of folding buffers listed in Table 1: 2500 ml of folding buffer 1 twice, each for 24 hrs; 2500 ml of folding buffer 2 twice, each for 12 hrs; 2500 ml of folding buffer 3 twice, each for 12 hrs; 2500 ml of folding buffer 4 twice, each for 12 hrs and 2500 ml of folding buffer 5 twice, each for 12 hrs. The final sample was dialyzed against 2500 ml of PBS for 3 times. To prevent lipid oxidation, all of the buffers should be purged with nitrogen gas.

was filtered with 0.22 μm membrane with gentle stirring at 4° C. for 1 hr and purged with nitrogen gas to avoid lipid oxidation. In addition, 2 mg of apolipoprotein B-100 was dissolved in 1 ml of denaturing buffer, and then filtered with 0.22 μm membrane, followed by mixing the dissolved apolipoprotein B-100 with the mixtures containing SPIO or M4N with gentle stirring at 4° C. for 1 hr. According to the "quasi-static over-critical folding path" method, the mixture was transferred into a dialysis tube and dialyzed against a series of folding buffers: 2500 ml of folding buffer 1 twice, each for 24 hrs; 2500 ml of folding buffer 2 twice, each for 12 hrs; 2500 ml of folding buffer 3 twice, each for 12 hrs; 2500 ml of folding buffer 4 twice, each for 12 hrs and 2500 ml of folding buffer 5 twice, each for 12 hrs. The final sample was dialyzed against 2500 ml of PBS for 3 times. To prevent lipid oxidation, all of the buffers should be purged with nitrogen gas.

EXAMPLE 8

Observation of LDL, rABL, Lipoprotein B-29/B-48 with Fluorescence Microscopy

ApoB polyclonal antibody (Roche, Brandford, Conn.) was coated on a cover glass at 37° C. for 1 hr. The antibody was blocked in PBS buffer containing 3% bovine serum albumin for 30 mins for avoiding non-specific binding. The samples, including LDL, rABL, folding intermediate of rABL, and apolipoprotein B-29/apolipoprotein B-48, were incubated and immobilized with apoB polyclonal antibody at 37° C. for 1 hr. The proteins, which are not bonded with the antibody on the cover glass, were washed with PBS. After adding apoB antibody (Santa Cluz) at 37° C. for 1 hr, and the remaining antibody was washed with PBS. The samples were then incubated with Cy3-conjugated secondary body to label apoB (Santa Cruz, Calif.) antibody. The lipids were stained using 3,3'-dioctadecyloxacarbocyanine perchlorate (DiO;DiOC18(3), Invitrogen). The fluorescence of apoB protein and lipids was observed with fluorescence microscopy and recorded using CCD camera.

TABLE 1

Chemical compositions of denaturing and folding buffers

| | Tris (mM) | pH | Urea (M) | DTT (mM) | Mannitol (%) | Pefabloc (μM) | Detergent (BS) (%) |
|---|---|---|---|---|---|---|---|
| Denaturing buffer | 10 | 11 | 6 | 100 | 0.1 | 1 | 5 |
| Folding buffer 1 | 10 | 11 | 2 | 0.1 | 0.1 | 0.1 | 0.5 |
| Folding buffer 2 | 10 | 11 | 1 | 0.1 | 0.1 | 0.1 | 0.1 |
| Folding buffer 3 | 10 | 11 | — | 0.1 | 0.1 | 0.1 | 0.02 |
| Folding buffer 4 | 10 | 8.8 | — | 0.1 | 0.1 | 0.1 | — |
| Folding buffer 5 | 10 | 8.8 | — | 0.1 | — | 0.1 | — |

EXAMPLE 7

Preparation of Lipoprotein B Lipoparticles Containing SPIO and M4N (Hereinafter Referred to SPIO@rABL and M4N@rABL)

SPIO and M4N were dissolved in the danaturing buffer respectively and prepared as denaturing buffers containing SPIO (final concentration 100 μg/ml of iron ions) and M4N (final concentration of 10 mM), meanwhile, 6.5 mg of lipids were dissolved in 1 ml of denaturing buffer. Finally, buffer containing SPIO or buffer containing M4N was mixed with lipids pre-dissolved in the denaturing buffer. The mixture

EXAMPLE 9

Analysis of rABL, SPIO@rABL and M4N@rABL Particle Size

The concentrations of the samples including rABL, SPIO@rABL and M4N@rABL were adjusted to 0.2 mg/ml and analyzed the particle size using dynamic light scatters (DLS). The DLS measurements were performed using a goniometer obtained from Brookhaven Instruments Corp. (Holtsville, N.Y.), equipped with a diode-pumped laser with a wavelength of 535.15 nm. The scattered light was collected at 90°. The chamber temperature was kept at 20° C. The particle size was calculated using non-negative least squares (NNLS).

EXAMPLE 10

Zeta Potential Measurements of rABL

The concentrations of the samples including rABL, SPIO@rABL and M4N@rABL were adjusted to 0.5 mg/ml and the zeta potential of the samples were analyzed using Delsa™ NanoC photon correlation spectrometer (Beckman Coulter Inc., Brea, Calif.).

EXAMPLE 11

Analysis of Drug Release Profile of rABL

SPIO@rABL and M4N@rABL were transferred into a dialysis bag and dialyzed against PBS for 48 hrs. At particular time, PBS was obtained and then measured the concentrations of iron ion and M4N. The concentration of the released M4N can be absorbed at 280 nm. For iron ion quantification, 100 µl of 12 N HCL was added with 100 µl of sample at room temperature (RT) for 30 mins, followed by incubated in the oven for 1 hr. 200 µl of 1% ammonium persulfate (APS) was added to the previous mixture and 400 □l of 0.1M potassium thiocyanate (KSCN) was then added at room temperature for 5 minutes. Finally, the concentration of iron ion was determined at 495 nm.

EXAMPLE 12

Composition Analysis of rABL, SPIO@rABL and M4N@rABL

After the samples were dried and mixed with KBr, the compositions of rABL, SPIO@rABL and M4N@rABL were analyzed by Fourier transform infrared spectroscopy (PerkinElmer Spectrum 100 FTIR spectrometer (PerkinElmer, Waltham, Mass.)). Each readings was obtained by 32 scans at a resolution of 4 $cm^{-1}$ and the scanning range is 4000-450 $cm^{-1}$.

EXAMPLE 13

Observation of Cellular Uptake

Monocyte cell line THP-1 (hereinafter referred to THP-1) and Non-small cell lung cancer cell line A549 (hereinafter referred to A549) were cultured in RPMI-1640 medium (Invitrogen, Carlsbad, Calif.) supplemented with 10% fetal bovine serum, 100 U/ml penicillin and 10 □g/ml streptomycin.

EXAMPLE 14

Observation of Cellular Uptake

After the THP-1 and A549 cell lines were cultured in the serum-free medium for 16 hrs, LDL and rABL was added to the cells and cultured in the incubator for 11 hrs. The cells were harvested via centrifugation (10 min, 200×g, RT) and washed twice with PBS to remove free LDL and rABL. The cells were then fixed with 4% paraformaldehyde, and the cell membrane was permeabilized with 0.2% Triton X-100. ApoB, nuclei, and actin were stained with apoB antibody (Santa Cruz Biotechnology, Inc.), Hoechst 33342 and phalloidin-conjugated antiactin antibody, respectively. The cellular uptake was observed using a confocal microscope.

EXAMPLE 15

Cytotoxicity Test

After the THP-1 and A549 cell lines were cultured in the serum-free medium for 16 hrs, LDL and rABL (at the final concentrations of 5, 10, 20 □g/ml) were added to the cells and cultured in the incubator for 11 hrs. The trypan blue exclusion method was used to determine cell viability, wherein at least 400 cells were counted in each experiment.

EXAMPLE 16

LDL Receptor Competition Test

After the THP-1 and A549 cell lines were cultured in the serum-free medium for 16 hrs, anti-LDLR antibody was added into the cells and cultured for 1 hr. The anti-LDLR antibody was dialyzed against PBS twice to remove sodium azide. The cells were washed twice with PBS to remove non-binding anti-LDLR antibody in the medium. The rABL and LDL (at the final concentration of 10 □g/ml) were added into A549 cell lines and cultured in the incubator for 5 hrs. After removing medium, the cells were washed twice with PBS to remove the rABL and LDL that was not internalized by cells in the medium. The cells were then fixed with 4% paraformaldehyde. The cell membrane was permeabilized with 0.2% Triton X-100. ApoB, cell skeleton and nuclei were stained with anti-apoB antibody, phalloidin-conjugated anti-actin antibody and Hoechst 33342, respectively, and then observed by a fluorescence microscope.

EXAMPLE 17

Western Blot Analysis of Cell Metabolic Responses

After the THP-1 and A549 cell lines were cultured in the serum-free medium for 8 hrs, rABL (at the final concentration of 20 □g/ml), LDL (at the final concentration of 20 □g/ml) and oxaliplatin (at the final concentration of 10 □g/ml) were added into the cells, respectively and then cultured in the incubator for 11 hrs. After the cells were lysed, the expressions of these proteins were detected using anti-HMGR, anti-p53, anti-p-p53 (ser-15), anti-Erk, anti-p-Erk, anti-p38 anti-p-p38, anti-caspase 3 and anti-actin antibodies by the conventional Western blot procedure.

EXAMPLE 18

Electron Microscopy Imaging of SPIO@rABL and LDL with SP-HRTEM

A solution-phase high-resolution transmission electron microscope (hereinafter referred to SP-HRTEM) was used in the present invention, and 0.5 □l of samples (rABL and LDL encapsulated with SPIO) were sealed in a self-aligned wet (SAW) cell. The morphology of the sample was observed using a field emission gun ((FEG)-TEM, JEM-2010F, JEOL, Tokyo, Japan).

EXAMPLE 19

In Vivo MRI Imaging Examination

300 □l of SPIO@rABL containing 250 □g/ml iron ions (at the final concentration of iron ion in mice is 5 mg/kg) and 500 LDL were injected into 4-5 weeks old BALB/c mice by an intravenous administration. Sequential MRI acquisition was performed using a 9.4-T MR imager (Bruker Biospec 94/20 USR). ParaVision 5.0 and Matlab 6.0 were used to analyze the MRI image signal intensities. The Signal-to-noise ratio (SNR) of the liver was calculated using the following formula:

SNR=signal intensity of the liver/SD of the background noise     (1)

EXAMPLE 20

Functional Test of M4N@rABL

Figure 2:
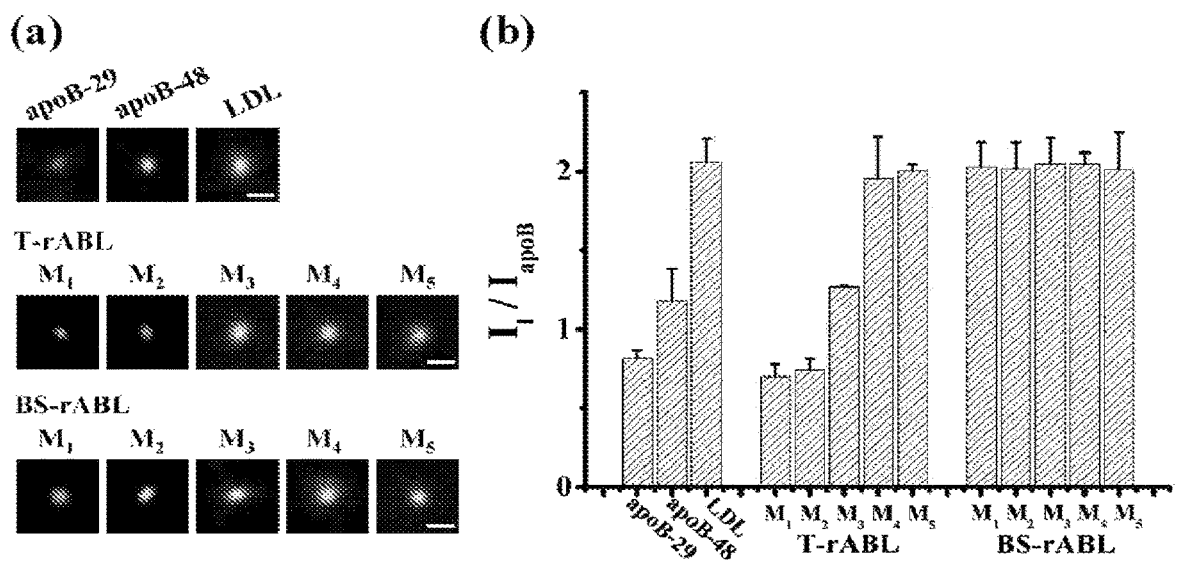
FIG. 2 shows fluorescence images of LDL and reconstituted apolipoprotein B lipoparticles. (a) upper figure: apolipoprotein B-29/B-48 and low density lipoprotein; center figure: folding intermediate of reconstituted apolipoprotein B lipoparticle (hereinafter referred to T-rABL) with addition of Triton X-100; lower figure: folding intermediate of reconstituted apolipoprotein B lipoparticle (hereinafter referred to BS-rABL) with the addition of deoxycholic acid; (b) The quantified diagram of FIG. Red image denotes lipoprotein B; green image denotes lipid. The scale bar is 1 □m.

After the A549 cell line was cultured in the serum-free medium for 16 hrs, LDL (at the final concentration of 20 □g/ml), M4N (at the final concentration of 100 □M), M4N@rABL (at the final concentration of 20 □g/ml of rABL and 100 □M of M4N), and M4N@rABL (at the final concentration of 20 □g/ml of rABL and 100 □M of M4N) with LDL (at the final concentration of 40 □g/ml) were added into the cell respectively and cultured for 24 hrs. After removing the medium, the cells were washed twice with PBS and cultured with serum-containing medium for 48 hrs. The cell viability was observed by a trypan blue staining.
Statistical Analysis All the quantitative assays were carried out in 3-10 replicates and the data were expressed as mean±standard error of the mean (SEM). A P value less than 0.05 was considered statistically significant.
Results and Discussion
1. Preparation of Apolipoprotein B As shown in FIG. 1, apolipoprotein B was obtained after LDL was isolated from human plasma via an ultra centrifugation (d=1.062-1.063 g/ml) followed by extracted from an ice-cold methanol/ether mixture. In the present invention, 20 to 40 mg of apolipoprotein B (20-40 mg/dl) can be obtained from one liter of serum. For the expression of apolipoprotein B29/B48, after the proteins were expressed in a prokaryotic expression system by IPTG induction, the strains were obtained. The strains were lysed by a high pressure disruptor and the supernatants were performed an ultra centrifugation to obtain apolipoprotein B-29/B-48.
2. In Vitro Folding of Apolipoprotein B Using a Quasi-Static Over-Critical Folding Path In order to prevent precipitation of apolipoprotein B-100 due to dramatic environment changes during a folding process, a modified quasi-static over-critical folding path was used to refold apolipoprotein B in the present invention. The folding buffers were divided into 5 parts. The object is to change the environment slowly by dialysis, and thereby collect folding intermediates and observe any aggregation between apolipoprotein B-100 and lipids. The binding proportion of apolipoprotein B and lipids was quantified semiempirically by immuno-staining fluorescence microscopy. As shown in FIG. 2, from fluorescence imaging, the ratio of fluorescence intensity between rABL with addition of deoxycholic acid (hereinafter referred to BS-rABL) and apolipoprotein B (hereinafter referred to apoB) is 2.01±0.23 ($I_1/I_{apoB}$), the ratio of fluorescence intensity between rABL with addition of Triton X-100 (hereinafter referred to T-rABL) and apoB is 2.00±0.04, which is similar to the ratio of LDL (2.06±0.14). This represents whether it utilizes Triton X-100 or deoxycholic acid during the folding process, both of Triton X-100 or deoxycholic acid can assist B-100 restoring into LDL. Analysis of folding intermediates shows that rABL folded by using deoxycholic acid has two-state transition, and it reveals similar results with LDL from the initial folding state. There is no dramatic change until the last folding state. It indicates that rABL folded by using deoxycholic acid changes directly from the denaturing state to the refolding state without any intermediate state. As shown in FIG. 2, rABL folded by using Triton X-100 shows a different result, and only very few lipids aggregate with B-100. The closer the folding buffer to a natural buffer state, the more lipids aggregate with apolipoprotein B-100 (M1: 0.70±0.08, M2: 0.74±0.07, M3: 1.27±0.01, M4: 1.96±0.26, M5: 2.00±0.04). It indicates that the binding between Triton X-100 and apolipoprotein B-100 is replaced gradually with the one between lipids and B-100 during folding process. The ratio between the lipids of apolipoprotein B-29/B-48 and apolipoprotein B is 0.82±0.05 and 1.18±0.20, respectively, and it represents that apolipoprotein B-29 and B-48 expressed in a prokaryotic expression system also contain a part of lipids.

In order to further determine the exact ratio of lipids and apolipoprotein B, in the present invention, the cholesterol and protein were quantified to calculate the ratio thereof. As shown in Table 2, the ratio of the lipid of rABL and apolipoprotein B is 1.978±0.102, and the ratio of the lipid and apolipoprotein B is 1.968±0.073. In addition, after preparations of rABL were completed, the rABL was stable and can be stored at 4° C. for several months.

TABLE 2

Cholesterol/lipid ratios in LDL and rABL

|  | Protein (apoB) Unit(□g/ml) | Cholesterol Unit (□g/ml) | Ratio |
|---|---|---|---|
| LDL | 241.81 ± 12.17 | 478.41 ± 5.34 | 1.978 ± 0.102 |
| rABL | 242.66 ± 8.41 | 477.59 ± 6.31 | 1.968 ± 0.073 |
| Reference |  |  | 1.957 |

3. Cell Cytotoxicity of rABL

Figure 3:
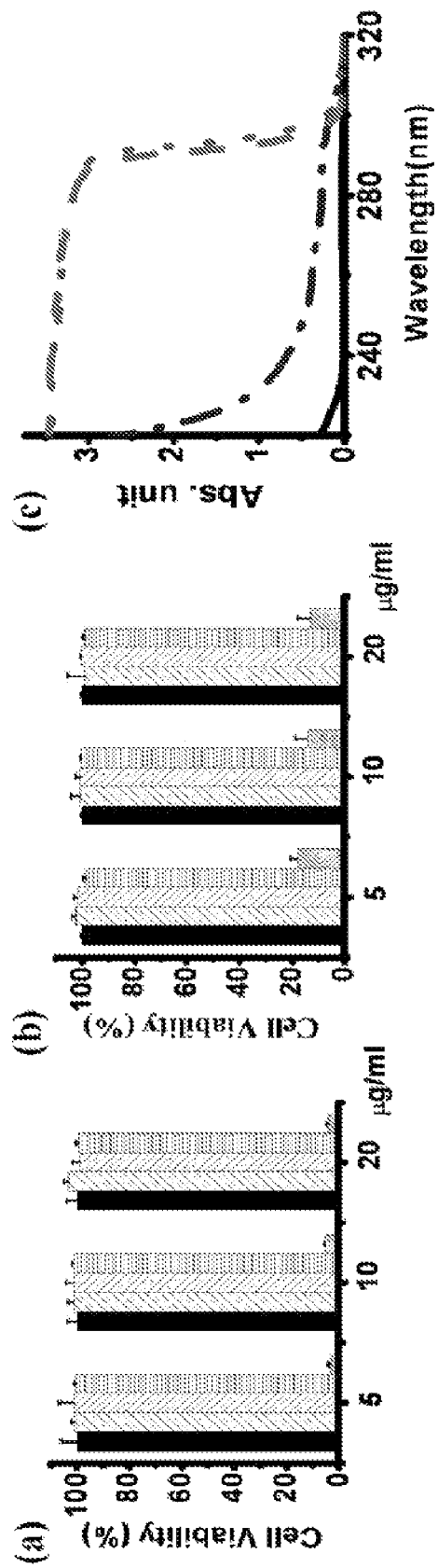
FIG. 3 shows cytotoxicity test. After culturing THP-1 (a) and A549 (b) with different concentrations (5, 10, 20 □g/ml) of LDL and reconstituted apolipoprotein B for 11 hrs, then stained with Trypan blue and calculate cell viability. ■: addition of PBS; ▨: addition of Triton X-100 followed by dialysis against PBS during folding; ▨: addition of LDL; ▤: addition of BS-rABL; ▨: addition of T-rABL; (c) 1% of Triton X-100 under UV-vis measurement (dashed line); BS-rABL with Triton X-100 (dotted line); LDL (dashed-dotted line); addition of Triton X-100 followed by dialysis against PBS (solid line).
Figure 4:
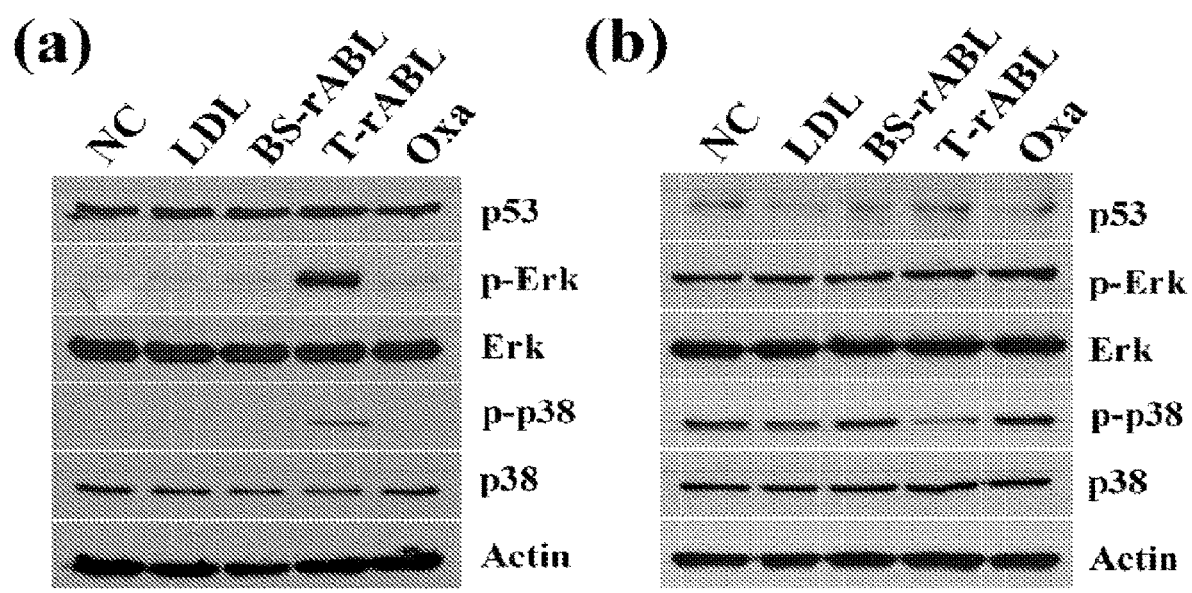
FIG. 4 shows cytotoxicity analysis with addition of Triton X-100 of A549 (a) and THP-1 (b) after adding T-rABL in Triton X-100. NC is control group with addition of PBS only. Oxa is oxaliplatin.
Figure 5:
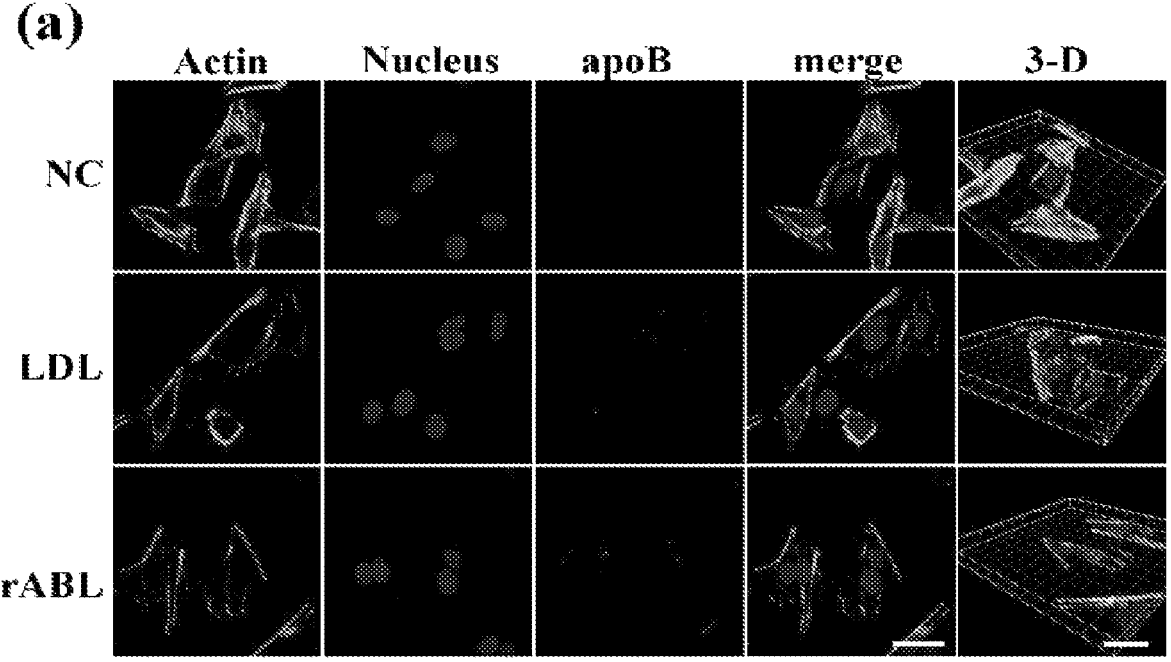
FIG. 5 shows cellular uptake of rABL. A549 (a) and THP-1 cell (b) were treated with PBS (NC), LDL, rABL for 11 hrs. Blue part is the cell nucleus; red part is apolipoprotein B; and green part is actin. The scale bar is 30 □m.
Figure 5:
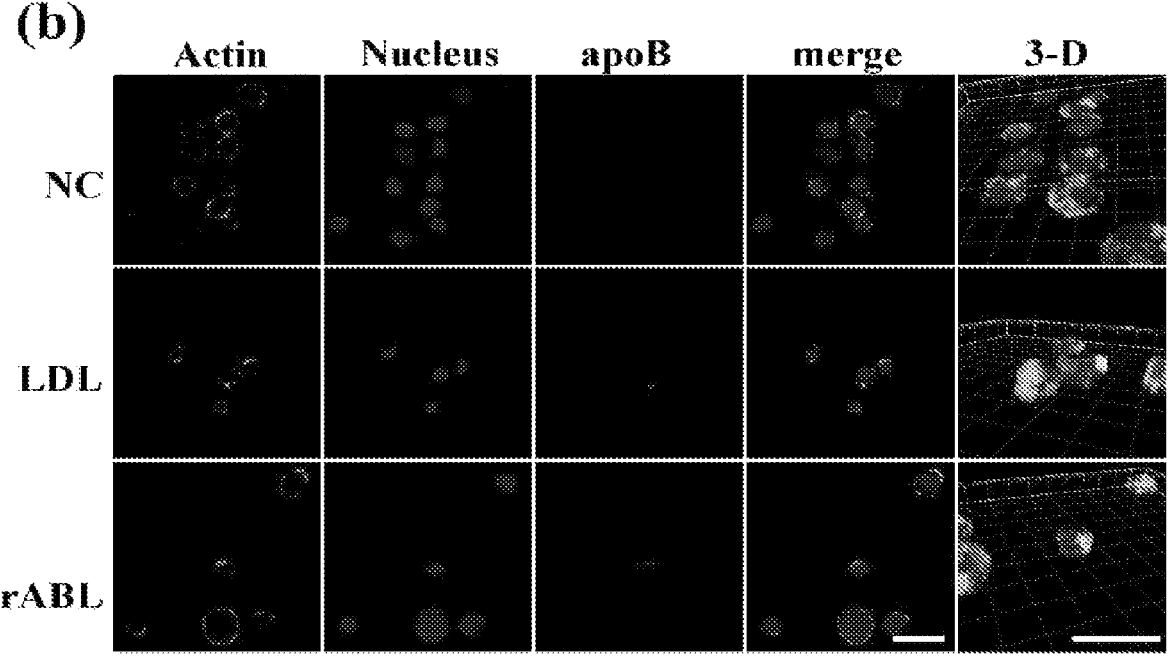

As shown in FIG. 3, THP-1 (see FIG. 3(a)) and A549 (see FIG. 3(b)) cell lines were used to test the cytotoxicity of T-rABL and BS-rABL. After the rABL and LDL (at the final concentrations of 5, 10, 20 □g/ml) were added into THP-1 and A549 cells, the cells were cultured at 37° C. for 11 hrs. The cells were then stained with Trypan blue to discriminate living cells and dead cells. In the present invention, T-rABL shows significant cytotoxicity while BS-rABL and LDL show no significant cytotoxicity. As shown in FIG. 3C, in the profile analysis, there are still some residues of Triton X-100 in T-rABL.
4. Cytotoxicity Analysis of T-rABL In order to confirm the cytotoxicity is derived from residues of Triton X-100, T-rABL was added to A549 (see FIG. 4(a)) and THP-1 cells (see FIG. 4(b)) and cultured for 1 hr, followed by Western Blotting analysis. In A549 cells, the expression amounts of p-p38 and p-ERK were increased upon T-rABL, and it suggests that the cytotoxicity is caused by changes of the osmotic pressure and led to the activation of MAPK path and cause cell death. However, In BS-rABL group, there is no difference between BS-rABL group and LDL.
5. Analysis of Cellular Uptake of rABL Since the above results show T-rABL has a severe cytotoxicity, all of the following physiological experiments use BS-rABL. Besides, in order to confirm whether rABL functions as same as LDL, A549 (see FIG. 5(a)) and THP-1 (see FIG. 5(b)) cell lines were used to determine if rABL is internalized by the cells. The rABL and LDL at the final concentration of 100 μg/ml were added in A549 and THP-1 cells and cultured at 37° C. for 11 hrs. The results of the cellular uptake for rABL and LDL were observed by the confocal microscope. As shown in FIG. 5, both of rABL and LDL can be internalized by A549 and THP-1 cells and has a similar distribution.

6. LDL Receptor Mediated Endocytosis of rABL

Figure 6:
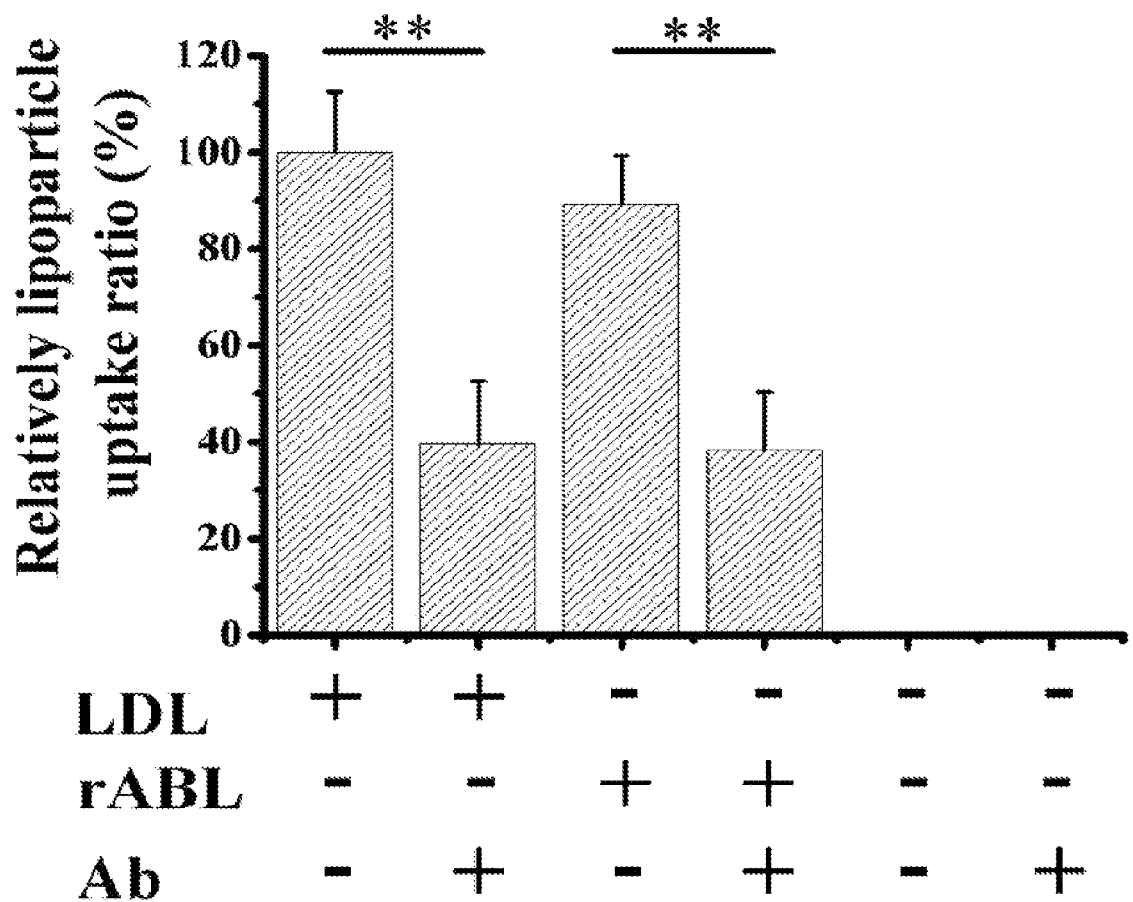
FIG. 6 shows the LDLR competition test for LDL and rABL. Ab is anti-LDLR antibody. Control group has added same amounts of PBS. **P<0.01.

In order to further confirm that the rABL is recognized and internalized by the cells via receptor-mediated endocytosis, LDL receptor (hereinafter referred to LDLR) competition test was carried out using A549 cells. Since THP-1 cell has a scavenger receptor, it is not appropriate for this experiment. As shown in FIG. 6, after adding antibodies for LDLR, the ratio of the cellular uptake for the r-ABL and LDL were reduced dramatically, for example, r-ABL: 38.4±11.9%; LDL: 39.5±13.1%. It suggests that rABL and LDL can be recognized and internalized by the LDLR.

7. Western Blot Analysis of Cell Metabolic Responses

Figure 7:
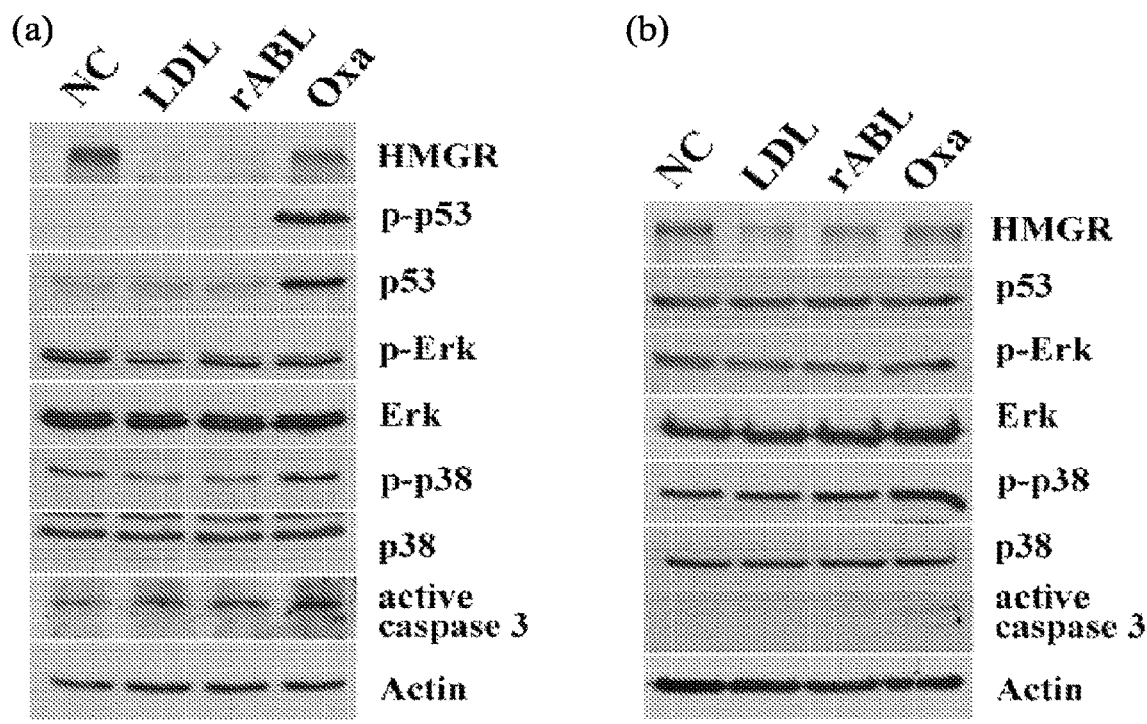
FIG. 7 shows the Western blot analysis of cell metabolic responses for LDL- and rABL (a) A549 and (b) THP-1 cell lines. NC is the control group. Oxa is oxliplatin.

A series of cellular metabolic responses will be triggered upon endocytosis of LDL. In order to confirm the similarity between rABL and LDL, after treating with rABL and LDL, cell lysates were collected and analyzed the differences of cell metabolic responses by Western blot analysis. As shown in FIG. 7, there is no significant difference on phosphorylation levels of oxidative stress response proteins such as p-p53 (ser-15), p-p38 and p-Erk while the activation level of apoptosis marker protein such as caspase 3 did not significantly increase. In addition, compared to the control group, after treating with rABL and LDL, the expression of cholesterol synthesis enzyme such as 3-hydroxy-3-methylglutaryl-CoA reductase (hereinafter referred to HMGR) is decreased. Combining the results shown in FIG. 6 and FIG. 7, it is confirmed that rABL can be recognized and internalized by the LDLR for providing cholesterol to the cells.

8. Development of rABL for Drug Delivery

Figure 8:
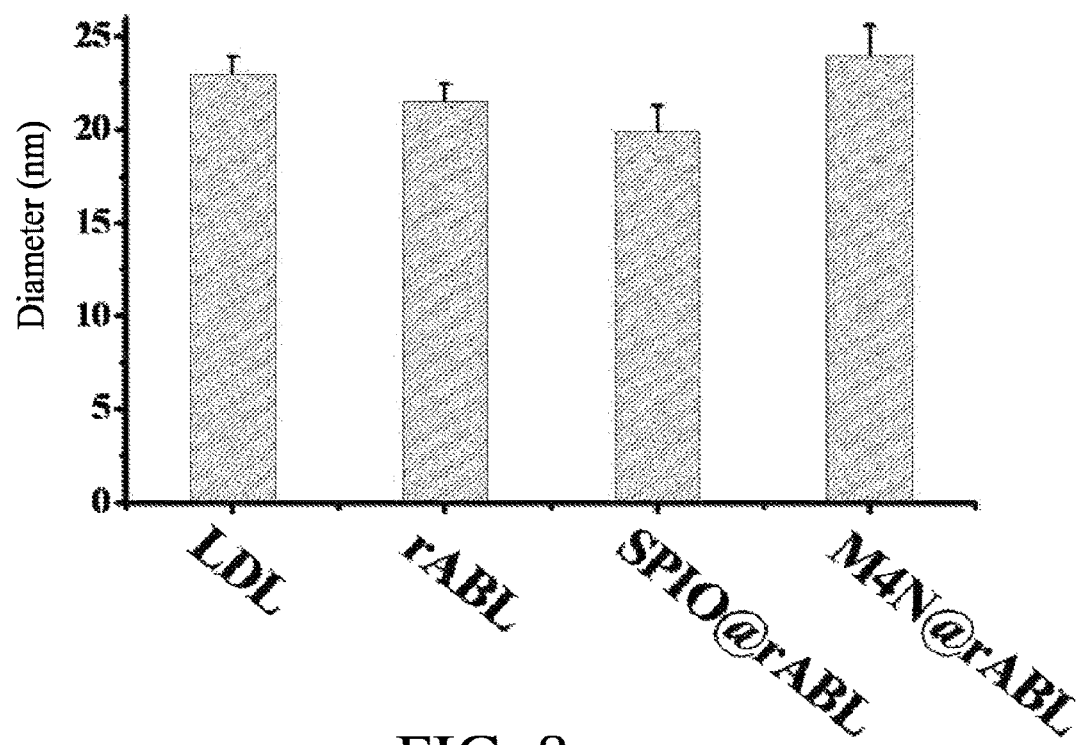
FIG. 8 shows the particle sizes of LDL, rABL, SPIO@rABL and M4N@rABL measured by DLS.
Figure 9:
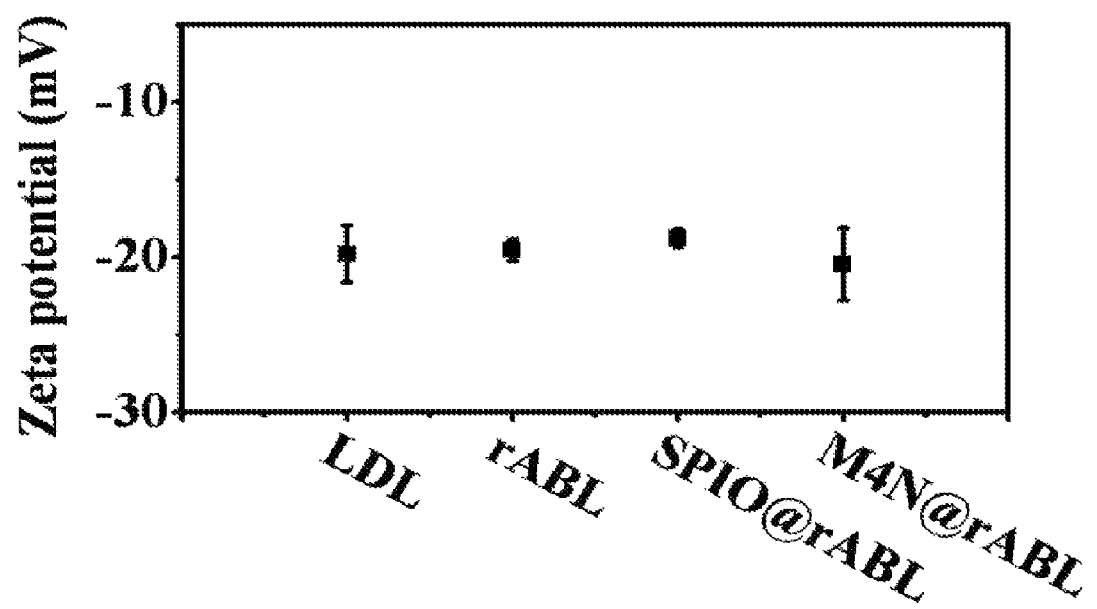
FIG. 9 shows the zeta potentials of LDL, rABL, SPIO@rABL and M4N@rABL.
Figure 10:
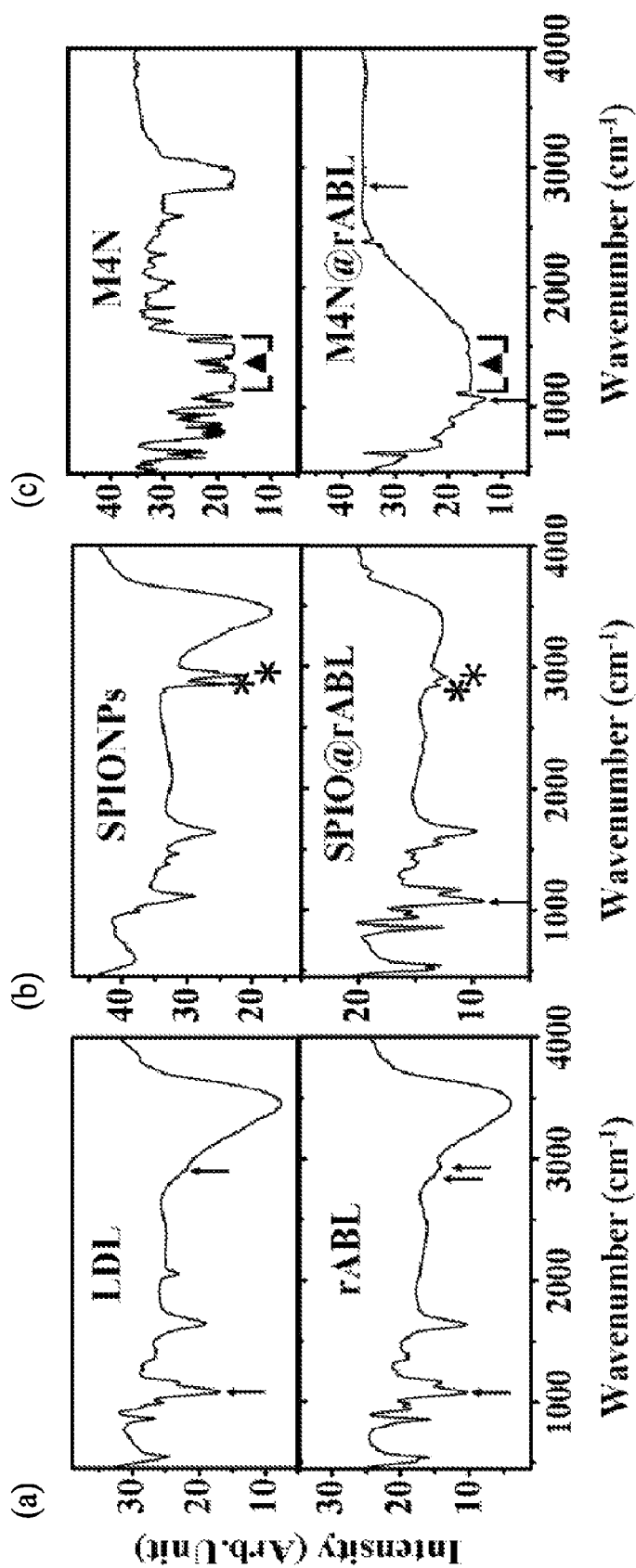
FIG. 10 shows the FTIR spectra of LDL and; rABL(a), SPIONPs; and SPIO@rABL(b), M4N and M4N@rABL(c). Stars, arrows, and triangles indicate signals from SPIONPs, protein/lipid, and M4N, respectively.
Figure 11:
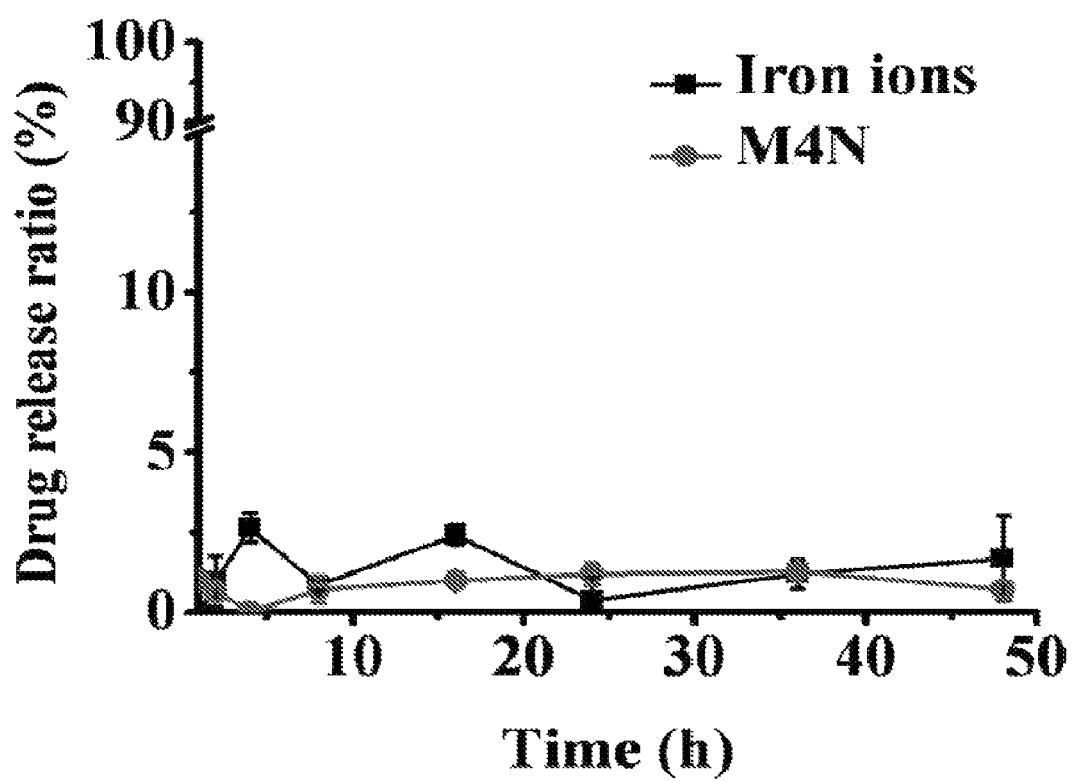
FIG. 11 shows the drug release profile measurements of iron ions and M4N. The relative concentrations of released iron ions and M4N were compared with rABL-incorporated iron ions and M4N (SPIO@rABL and M4N@rABL) at initial state.

After confirming the similarity of rABL and LDL, the present invention further determine whether rABL has the capability of carrying hydrophobic substances. The hydrophobic SPIO and lipophilic small molecule anticancer drug such as M4N (molecular weight of 358 Da) were added into the reconstituted mixture in the first step of rABL formation. After the preparation was completed, dynamic light scattering (DLS), Zeta Potential, and Fourier transform infrared spectroscopy (FTIR) were used to analyze the physical properties. In DLS measurement, the diameters of rABL, SPIO@rABL and M4N@rABL are 21.5±0.93, 19.9±1.33 and 23.9±1.6 nm, respectively. As shown in FIG. 8, such diameters are similar with those of LDL (i.e. 18 to 25 nm). As shown in FIG. 9, the zeta potential of LDL, rABL, SPIO@rABL and M4N@rABL are −19.8±1.84, −19.5±0.67, −18.79±0.56 and −20.5±2.32 mV, respectively. In FTIR analysis, as shown in FIG. 10 and Table 3, it is also confirmed that the compositions of rABL and LDL are similar, and SIPO and M4N were also successfully incorporated into rABL. In addition, since the rABL is desired to be used in drug delivery, it is critical to consider the stability of rABL. In the drug release profile analysis, as shown in FIG. 11, it is confirmed that SPIO@rABL and M4N@rABL are stable and the drugs are not easily released in PBS.

TABLE 3

Peaks assignment of Fourier transform infrared spectroscopy (FTIR) analysis of LDL, rABL, SPIO@rABL, M4N@rABL

| FTIR signal ($cm^{-1}$) | Distribution |
| --- | --- |
| 1080 | C—O (protein/phospholipids) |
| 621 | Fe—O |
| 2929, 2857 | APTES ($Fe_3O_4$) |
| 2854 | $CH_2$ symmetric stretch (mainly lipid) |
| 2928 | $CH_3$ symmetric stretch (mainly protein) |
| 1200-1600 | M4N |

9. SP-HRTEM Imaging of rABL

Figure 12:
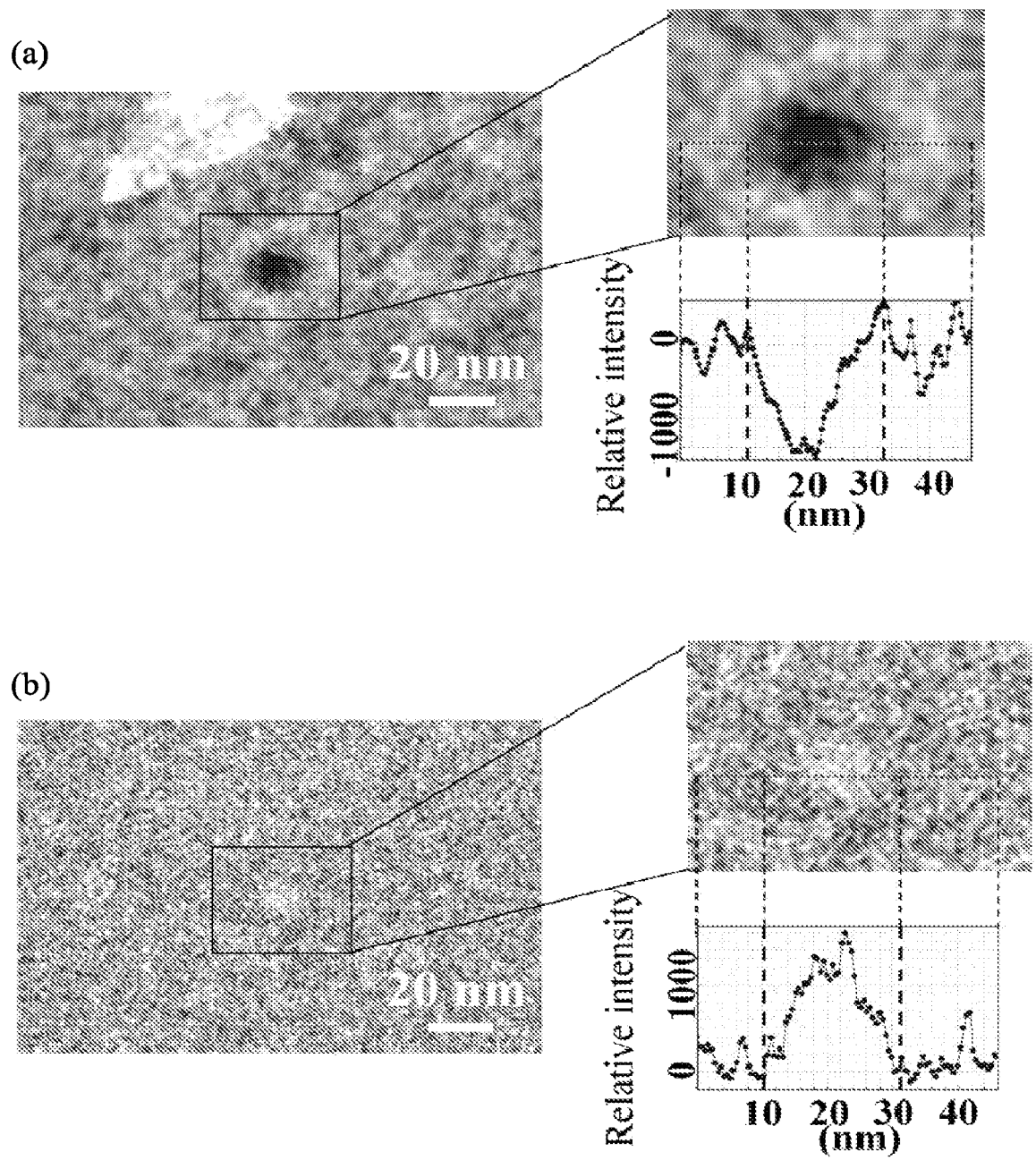
FIG. 12 shows (a) SP-HRTEM imaging used to identify SPIO@rABL containing a high electron density (scale bar is 20 nm). (b) LDL particle observed as a control is indicated with a black dot circle (scale bar is 20 nm).

In order to observe LDL and rABL at single-molecular level, a solution-phase high-resolution transmission electron microscope (SP-HRTEM) was used in the present invention. After SPIO was incorporated into rABL, due to the high electronic density of iron nanoparticles, a strong contrast image can be produced under SP-HRTEM. In contrast, as shown in FIG. 12, the contrast of image for LDL is weaker. In addition, the particle sizes of LDL and rABL are around 20 nm under SP-HRTEM and the results are as same as those observed by the dynamic light scattering (see FIG. 8).

10. SPIO@rABL Can be Used as T2 Contrast Medium

Figure 13:
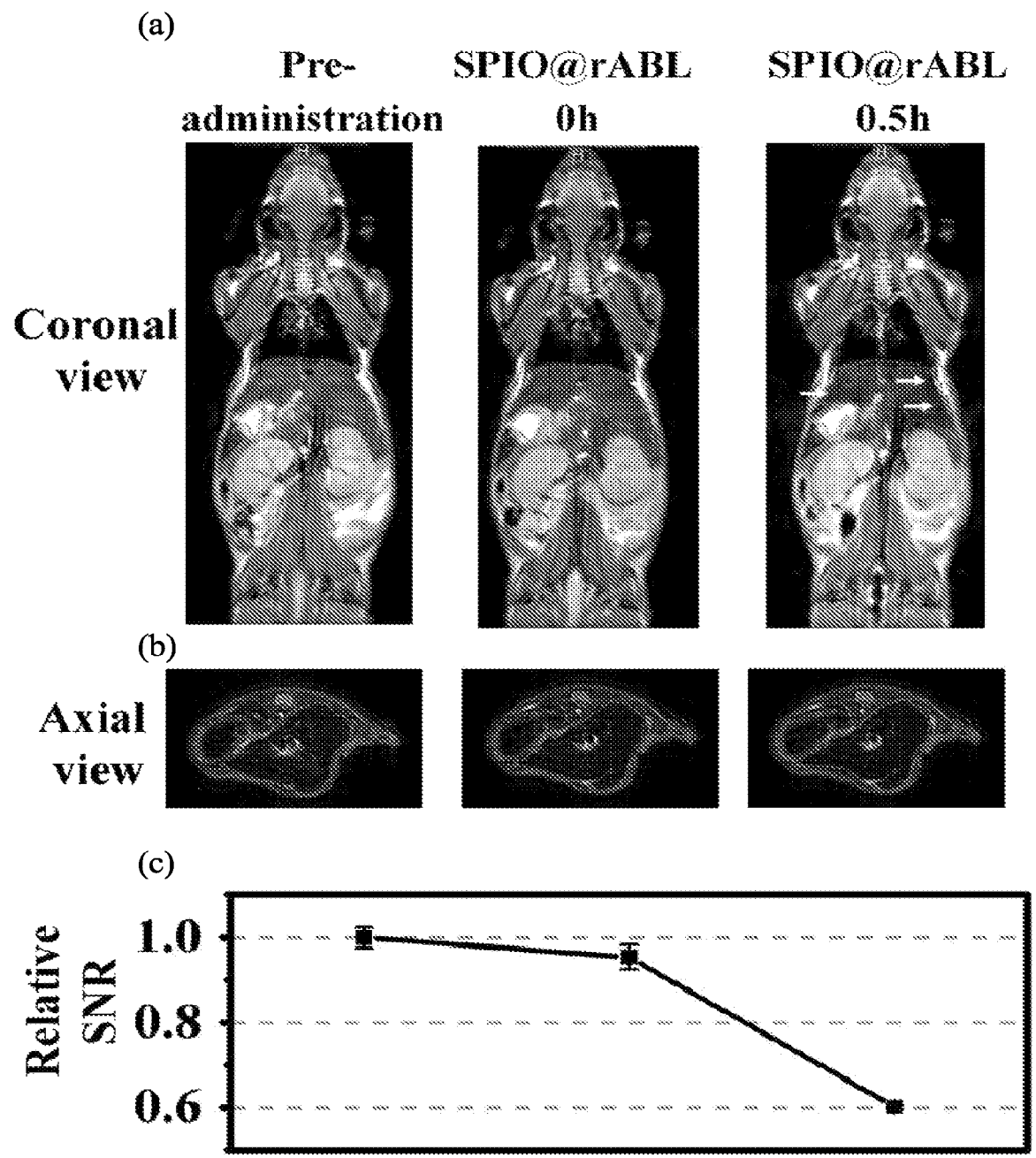
FIG. 13 shows in vivo imaging pattern of coronal view (a) and axial view (b) of SPIO@rABL contrast enhanced MRI in mice liver. The SPIO@rABL 0.5 h MRI image compared mice in the pre-administration state, whereas SPIO@rABL at 0 hr showed signal reduction (arrows) in liver (red circle) after APIO@rABL administration to mice. (c) Relative SNR was determined by computer-assisted analysis of MR images. For each mouse, 3 images were analyzed and mean of SNR was determined. The average SNR of pre-administration mice was 16.96±0.41.

After intravenous injection of SPIO@rABL (at the final concentration of 5 mg/kg) into mice, MRI acquisition was performed using 9.4-T MR imager. A half hour after the injection of SPIO@rABL, as shown in FIG. 13, it is found that the signal to noise (SNR) of the liver in mice was weaker. Since most of LDL is combined with the LDL of liver and then recycled, signals of T2 MRI of the liver was rapidly declined. Besides, the concentration of SPIO used in the present invention is about ¼ of the previous studies, and it will produce similar SNR decline value. This shows that rABL of the present invention has the potential for carrying the hydrophobic contrast medium.

11. Decreasing Cancer Cell Viability by M4N@rABL

Figure 14:
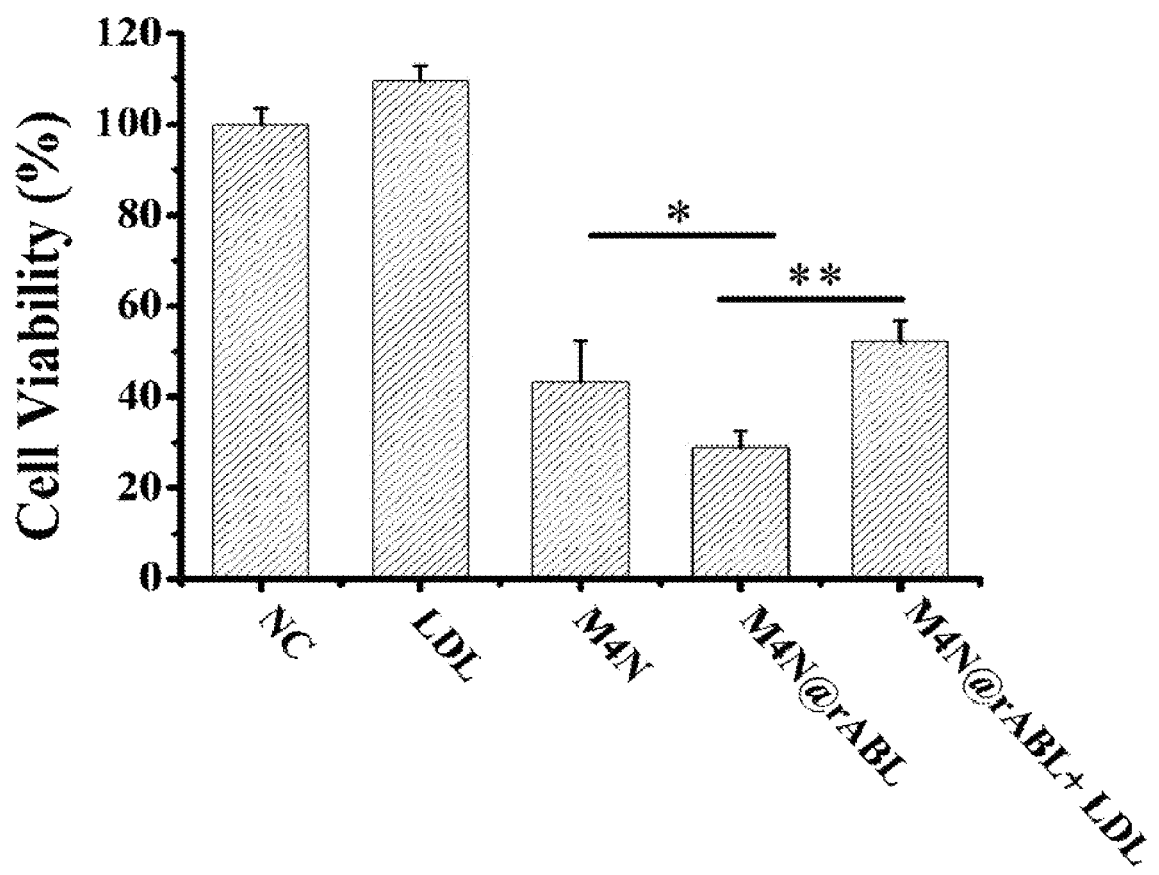
FIG. 14 shows the cell viability and competition test of LDL and M4N@rABL-treated A549 cancer cells. NC denotes the negative control represented by treatment with only PBS. **P<0.01.

In previous studies, M4N is found to lower the viability of cancer cells. In the present invention, A549 cells were treated with M4N and M4N@rABL. As shown in FIG. 14, the cells treated with M4N alone has 40% of cell viability, while the cells treated with M4N@rABL has even lower (30%) cell viability (i.e. 30%). This proves that M4N with the drug carrier has better effect in reducing cell viability of cancer cells. In addition, after adding additional LDL, the cell viability caused by M4N@rABL has increased (about 55%). It proves that M4N@rABL and LDL have the same endocytosis pathway.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

What is claimed is:

1. A method for preparing a reconstituted apolipoprotein B lipoparticle, comprising steps of:
 a) dissolving apolipoprotein B in a first buffer containing 1 wt % to 15 wt % amphiphilic compound and 2M to 8M urea to form a first mixture;
 b) dissolving lipid in a second buffer containing 1 wt % to 15 wt % amphiphilic compound and 2M to 8M urea to form a second mixture;

c) filtering the first mixture and the second mixture, respectively;
d) combining the first mixture and the second mixture to form a third mixture;
e) dialyzing the third mixture against a first folding buffer to reduce concentrations of the urea and the amphiphilic compound in the third mixture and obtain a first dialyzed mixture, wherein the concentration of the urea ranges from 0 to 2 M and the concentration of the amphiphilic compound ranges from 0 to 0.5 wt % in the first folding buffer;
f) dialyzing the first dialyzed mixture against a second folding buffer to reduce concentrations of the urea and the amphiphilic compound in the first dialyzed mixture and obtain a second dialyzed mixture, wherein the concentration of the urea ranges from 0 to less than or equal to 2 M and the concentration of the amphiphilic compound ranges from 0 to less than or equal to 0.5 wt % in the second folding buffer; and
g) repeating f) to stepwise reduce the concentrations of the urea and the amphiphilic compound,
wherein the lipid is at least one selected from the group consisting of phospholipid, cholesterol and triglyceride, and the amphiphilic compound is a non-ionic surfactant or bile acid.

2. The method of claim 1, further comprising steps of dissolving a hydrophobic substance in a buffer which has the same composition as the first buffer, in the step a), followed by filtering out the buffer having the hydrophobic substances.

3. The method of claim 2, wherein the hydrophobic substance is a contrast medium or a lipophilic drug.

4. The method of claim 3, wherein the contrast medium is at least one selected from the group consisting of superparamagnetic iron oxide nanoparticle, Mangafodipir, Gadoxetic acid, Gadopentetic acid, Gadobenic acid, Gadoteric acid and Vistarem.

5. The method of claim 3, wherein the lipophilic drug is at least one selected from the group consisting of tetra-O-methyl nordihydroguaiaretic acid (M4N), paclitaxel and doxorubincin.

6. The method of claim 1, wherein at least one of the first buffer and the second buffer has a pH value of 11.

7. The method of claim 1, wherein at least one of the first folding buffer and the second folding buffer has a pH value ranges from 8.8 to 11.

8. The method of claim 1, wherein the apolipoprotein B is natural apolipoprotein B or synthetic reconstituted apolipoprotein B.

9. The method of claim 8, wherein the apolipoprotein B is at least one selected from the group consisting of apolipoprotein B-100, apolipoprotein B-29 and apolipoprotein B-48.

10. The method of claim 1, wherein the non-ionic surfactant is Triton X-100.

11. The method of claim 1, wherein the bile acid is deoxycholic acid.

* * * * *